(12) United States Patent
Roxhed et al.

(10) Patent No.: US 9,304,100 B2
(45) Date of Patent: Apr. 5, 2016

(54) MINIATURISED ELECTROCHEMICAL SENSOR

(71) Applicants: Niclas Roxhed, Bromma (SE); Goran Stemme, Lidingo (SE); Hithesh K. Gatty, Lidingo (SE)

(72) Inventors: Niclas Roxhed, Bromma (SE); Goran Stemme, Lidingo (SE); Hithesh K. Gatty, Lidingo (SE)

(73) Assignee: AEROCRINE AB, Solna (SE)

( * ) Notice: Subject to any disclaimer, the term of this patent is extended or adjusted under 35 U.S.C. 154(b) by 552 days.

(21) Appl. No.: 13/744,533

(22) Filed: Jan. 18, 2013

(65) Prior Publication Data

US 2014/0202856 A1 Jul. 24, 2014

(51) Int. Cl.
*G01N 27/404* (2006.01)
*G01N 33/497* (2006.01)

(52) U.S. Cl.
CPC .......... *G01N 27/4045* (2013.01); *G01N 33/497* (2013.01)

(58) Field of Classification Search
CPC . G01N 27/304; G01N 27/406; G01N 27/407; G01N 27/48
See application file for complete search history.

(56) References Cited

U.S. PATENT DOCUMENTS 5,817,221 A * 10/1998 Leddy et al. .............. 204/290.06
2010/0120220 A1* 5/2010 Jung .............................. 438/429

FOREIGN PATENT DOCUMENTS

JP H04363653 A 12/1992
WO 01/36957 A1 5/2001

OTHER PUBLICATIONS

P. Jacquinot et al., "Amperometric Detection of Gaseous Ethanol and Acetaldehyde at Low Concentrations on an Au-Nafion Electrode", The Analyst, vol. 124, No. 6, dated Jan. 1, 1999.
Martina Nadherna et al., "A Planar, Solid-State Amperometric Sensor for Nitrogen Dioxide, Employing an Ionic Liquid Electrolyte Contained in a Polymetric Matrix", Sensors and Actuators B: Chemical, dated Jan. 1, 2012.
Fariborz Maseeh et al., "A Novel Silicon Micron Amperometric Gas Sensor", dated Jun. 24, 1991.
Joseph R. Stetter et al., "Amperometric Gas Sensors—A Review", Chemical Reviews, vol. 108 No. 2, dated Feb. 1, 2008.
European Search Report corresponding to App. No. 14446501.0-1554, dated Apr. 23, 2014.

\* cited by examiner

*Primary Examiner* — J. Christopher Ball
(74) *Attorney, Agent, or Firm* — Renner, Otto, Boisselle & Sklar, LLP

(57) ABSTRACT

A miniaturised electrochemical sensor for detection of a component in a gas is provided. The sensor comprises a reference electrode, a counter electrode and a structure comprising a plurality of passages delineated by walls extending along the passages. A working electrode covers the walls of the structure and a layer of an ionomer covers at least part of the working electrode along the walls of the structure. The layer of ionomer is in ion conducting contact with the electrodes. The disclosure further relates to a method of fabricating a miniaturised electrochemical sensor and to a device for measuring content of NO in exhaled breath comprising such a miniaturised electrochemical sensor.

29 Claims, 2 Drawing Sheets

MINIATURISED ELECTROCHEMICAL SENSOR

TECHNICAL FIELD

The present invention relates generally to a miniaturised electrochemical sensor for detection of a component in a gas, a device for measuring content of nitric oxide in exhaled breath comprising such a miniaturised electrochemical sensor and a method of manufacturing such a miniaturised electrochemical sensor.

BACKGROUND ART

In recent years, there has been an extensive investigation on NO as a biomarker. One such use of the biomarker is in the detection of respiratory inflammation such as asthma. The concentration of nitric oxide (NO) in exhaled breath serves as a marker of the inflammation in the airways of asthma patients. Thus the use of exhaled NO (eNO) is considered as a promising tool in diagnosing asthma. However, the concentration of eNO in the breath is very low. In a healthy adult the concentration is about 10-35 ppb (parts per billion) of NO whereas in children the concentration is about 5-25 ppb. An individual with considerable amount of inflammation has above 70-100 ppb.

Sensors using electrochemical methods to detect NO have previously been shown. However for measurements of exhaled NO, they lack the combination of fast response, small size and high sensitivity. Conventional electrochemical sensors can detect gas concentration down to some parts per billion but they suffer from long response times, typically in the order of 60-100 s. Consequently they require complicated flow handling and buffering of the exhaled breath sample.

SUMMARY OF INVENTION

An object of the present invention is to reduce the shortcomings discussed above and to provide a sensor for detection of a component in a gas having a high sensitivity and a fast response time.

It is also an object to provide a sensor that may be manufactured cost efficiently and that is small enough to be incorporated in hand held analysis devices.

Thus, the present disclosure relates to a miniaturised electrochemical sensor for detection of a component in a gas. The miniaturised electrochemical sensor comprises a reference electrode, a counter electrode and a structure comprising a plurality of passages delineated by walls extending along the passages. A working electrode covers the walls of the structure and a layer of an ionomer covers at least part of the working electrode along the walls of the structure. The layer of ionomer is in ion conducting contact with the electrodes, i.e. the reference electrode the counter electrode and the working electrode.

By arranging the working electrode and ionomer layer along the walls in the passages, a sensor having a large sensing area is provided. Thus the sensitivity of the sensor may be high while still maintaining a small size of the sensor. The construction with passages comprising a layer of ionomer also may provide a fast response time of the sensor.

The passages may have an aspect ratio of at least 0.25, at least 1, at least 4, at least 10, at least 20 or at least 50. Thus the sensing area may be larger or much larger than a corresponding planar sensor, and the sensitivity is directly dependent on the aspect ratio of the passages.

The passages may have a cross-sectional dimension in the range of 1-300 micrometers or in the range of 10-150 micrometers. Thus the passages may result in a large surface area of the structure while facilitating the deposition of the ionomer layer.

The surface area of the ionomer layer may be in the range of 2000-2 $cm^2$ per $cm^2$ foot print area or in the range of 1000-10 $cm^2$ per $cm^2$ foot print area or in the range of 200-20 $cm^2$ per $cm^2$ foot print area. The foot print area is defined in a plane perpendicular to the extension of the passages. Thus the sensitivity of the sensor may be high.

The sensor may comprise a first and a second surface, wherein the first surface is exposed to the gas and wherein the passages extend from the first to the second surface. Thus the passages may be exposed to gas at the first surface and to other parts of the sensor at the second surface.

The structure may be a porous structure, whereby the passages are formed as pores. The pores may extend in parallel throughout the structure. The pores may be provided in a close packed arrangement, and the close packed arrangement may be at least one of a hexagonal arrangement, a rectangular arrangement, a quadratic arrangement and a triangular arrangement. Thus a high surface area of the structure may be achieved.

The ionomer may be a sulfonated tetrafluoroethylene based fluoropolymer-copolymer, e.g. Nafion. The ionomer may be a proton conductor. The ionomer may be the Nafion product SE-5112 as obtainable from DuPont. Thus the sensor may be provided with a high sensitivity to the component in the gas.

The thickness of the ionomer layer covering the working electrode may be in the range of 10-2000 nm or 100-1000 nm or 300-700 nm. Thus a short response time of the sensor may be reached.

The ionomer may comprise a nanostructured solid material. Thus the effective surface area of the layer, at a microscopic level, may be very high, further increasing the sensitivity of the sensor.

The sensor may further comprise a liquid electrolyte in contact with the layer of ionomer and the reference and counter electrodes. Thus the sensor may be made less sensitive to variations in humidity in the ambient gas, and the long term stability of the sensor may be improved. The second surface of the structure may be in contact with the liquid electrolyte to allow the layer of ionomer on the walls of the passages to be in contact with, to be wetted by or to be humidified by the liquid electrolyte.

The sensor may comprise an enclosure for a volume of the liquid electrolyte. Thus the liquid electrolyte may be encapsulated in the sensor to improve the handling of the sensor.

The structure may formed by micromachining. The structure may be formed by micromachining of a silicon material. Thus the structure may be provided with features in the micrometer range, to yield a high surface area. The structure may further be batch fabricated and produced at a reduced cost.

The working electrode may comprise a material selected from the group consisting of platinum, gold, palladium, carbon and ruthenium.

The working electrode may be insulated from the structure by an insulating layer. The insulating layer may comprise a material selected from the group consisting of Al2O3, $SiO_2$, HfO2 and LaO. Thus the electrode area is confined to the passages and the surfaces of the structure.

The component in the gas may be NO. Thus the sensor may be used to analyse levels of exhaled NO in breath, as a biomarker for e.g. asthma.

The present disclosure further relates to a device for measuring content of NO in exhaled breath comprising a miniaturised electrochemical sensor according to the disclosure herein.

The present disclosure further relates to a method of fabricating a miniaturised electrochemical sensor as disclosed herein, comprising
providing a structure comprising a plurality of passages delineated by walls extending along the passages,
covering the walls of the structure with a working electrode,
depositing a layer of ionomer covering at least part of the working electrode along the walls of the structure.

The structure may be provided by etching a silicon material, preferably by deep reactive ion etching a silicon material. Thus structures having passages with very high aspect ratios AR, up to 100 and beyond may be fabricated.

The miniaturised electrochemical sensor may be batch fabricated using silicon microfabrication.

The layer of ionomer may be deposited by dip coating and desiccated under low pressure. Thus the layer of ionomer may be deposited inside the passages in a simple manner.

The working electrode may be deposited by atomic layer deposition. Thus the electrode may be deposited inside the passages, covering the walls of the passages, even at very high aspect ratios of the passages.

The method may further comprise:
providing a liquid electrolyte in electrical contact with the working electrode,
providing a reference electrode and a counter electrode in electrical contact with the liquid electrolyte.

BRIEF DESCRIPTION OF DRAWINGS

The invention is now described, by way of example, with reference to the accompanying drawings, in which.

DESCRIPTION OF EMBODIMENTS

In the following, a detailed description of a miniaturised electrochemical sensor for detection of a component in a gas is disclosed.

Figure 1:
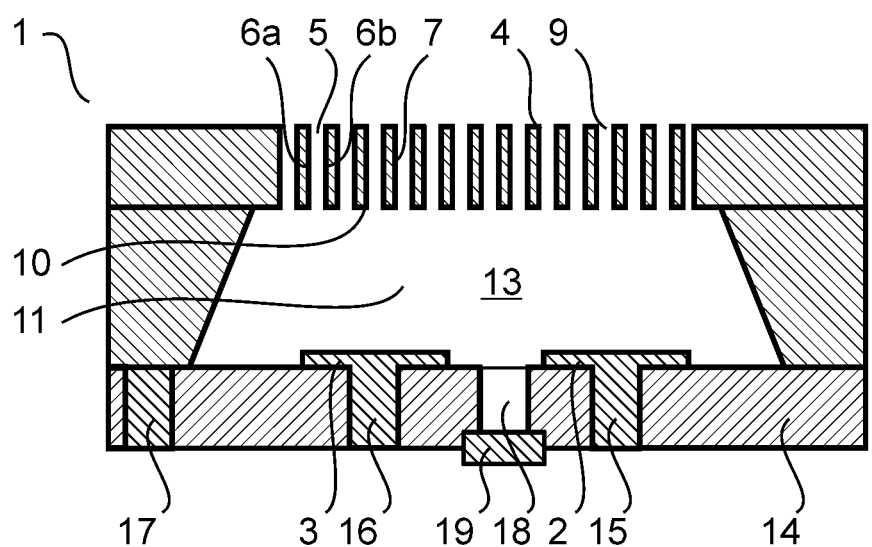
FIG. 1 shows a cross-sectional view of a miniaturised electrochemical sensor.

In FIG. 1 a miniaturised electrochemical sensor 1 for detection of a component in a gas is shown. The component in the gas may be a gaseous component such as NO. The sensor is an amperometric electrochemical sensor and comprises a reference electrode 2, a counter electrode 3 and a working electrode 7. The reference electrode and the counter electrode are supported by a substrate 14 formed in a material such as plastic (polycarbonate etc.) glass, ceramic, or silicon. The counter electrode is made of silver (Ag) and the reference electrode of silver which is oxidized ($AgO_2$). The electrodes may be provided with electrical vias 15, 16 and 17 for providing electrical contact through the substrate, as further disclosed in WO 2011073393 A2. The sensor further comprises a structure 4 having a first 9 and a second 10 surface and forming a grid comprising a plurality of passages 5 extending throughout the structure, from the first surface to the second surface. The passages 5 are formed as pores delineated by walls (6a, 6b) extending along the passages. The sensor forms a chamber 13, contained by the substrate 14 and the second surface of the structure 4, which chamber comprises liquid electrolyte 11 such as a mild acid solution (e.g. 10% $H_2SO_4$ (aq)). Thus the second surface of the structure faces the chamber 13 and is in contact with the liquid electrolyte. A gap of about 500 micrometers is maintained between the second surface of the structure with the working electrode and the counter/reference electrode by using a spacer. The substrate 14 may be provided with a through-hole 18 for supply of liquid electrolyte into the chamber. This may be used to compensate for any evaporation of liquid electrolyte through the passages in the structure. The through-hole may be sealed by a plug 19 as further disclosed in WO 2011073393 A2.

Figure 2:
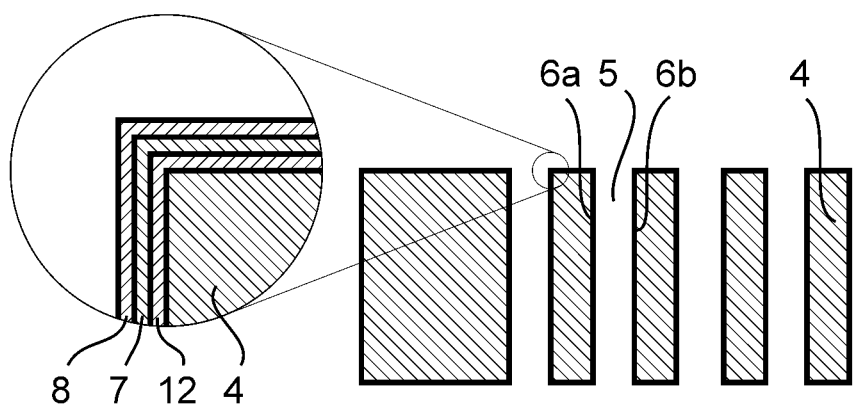
FIG. 2 shows a close up of part of a structure in a miniaturised electrochemical sensor.

In FIG. 2, the structure 4 defining passages 5 delimited by the walls 6a, 6b, is shown in further detail. The passages may be straight pores arranged in parallel and distributed over the structure 4. The structure 4 supports the working electrode 7 which covers the walls 6a, 6b of the structure and thus extends along the passages 5 from the first surface 9 to the second surface 10. The working electrode further covers at least a portion of the first 9 and second 10 surface to electrically connect the electrodes in the passages and form a working electrode having a large surface area. The structure 4 may be formed in single crystalline silicon and the working electrode in platinum (Pt). The working electrode is electrically insulated from the structure by means of an insulating layer 12 covering the structure forming the passages.

The portion of the structure provided with passages may cover an area of some $mm^2$, such as 6×6 $mm^2$. The passages may have cross-sectional dimensions in the range of 1-300 micrometers, or in the range of 10-150 micrometers, typically about 120 micrometers. The width of the walls of the grid defining the passages may be in the range of 1-100 micrometers, typically about 20 micrometers. The length of the passages may be in the range of 10-2000 micrometers, or in the rage of 50-850 micrometers, typically about 300 micrometers. The term aspect ratio (AR) is defined as a ratio of height (h) to width (w) of a structure or passage, i.e. AR=h/w. Thus the aspect ratio AR of the passages may be at least 0.25, at least 1, at least 4, at least 10, at least 20 or at least 50. A high AR may provide a large surface area of the walls defining the passages in the structure.

A layer 8 of a Nafion (SE-5112, Dupont, CAS number 31175-20-9) is deposited over the working electrode, in the passages 5, and over the surfaces 9 and 10. Nafion, a sulfonated tetrafluoroethylene based fluoropolymer-copolymer, is an ionomer which is selected to be a proton conductor (hydrogen ion, $H^+$). The material has the following structure;

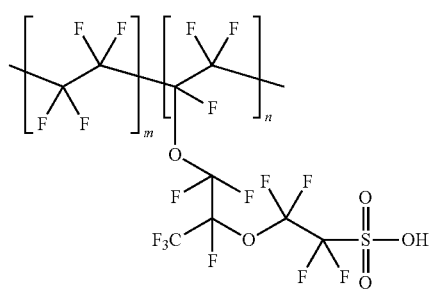

The layer of Nafion is about 100-1000 nm thick, or about 500 nm thick, and distributed over the walls of the passages. The layer of Nafion comprises particles having dimensions in the nanometer range, i.e. nanoparticles, which yield a very large surface area of the material. The layer of Nafion is in electrical contact with the counter electrode and reference electrode through the liquid electrolyte.

Figure 3:
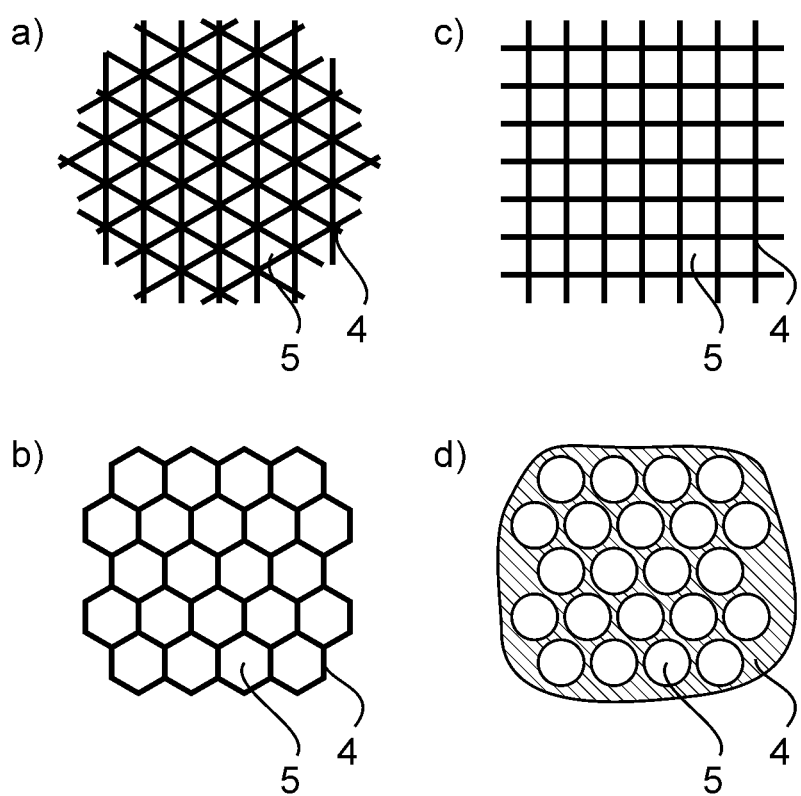
FIG. 3 shows various arrangements of passages in a miniaturised electrochemical sensor.

In FIG. 3, four different arrangements of passages and walls are disclosed. FIG. 3a shows an arrangement of passages 5 having a triangular cross-section in the structure 4. The passages are defined by walls arranged at angles of 60 degrees with respect to reach other. Thus every passage 5 is defined by three walls extending along the passage. FIG. 3b shows an arrangement of passages 5 having a hexagonal cross-section in the structure 4. The passages 5 are thus defined by six walls arranged at angles of 120 degrees with respect to reach other. FIG. 3c shows a quadratic arrangement of passages 5 in the structure 4. The passages are defined by walls arranged at right angles with respect to reach other. Thus every passage 5 is defined by four walls extending along the passage. FIG. 3d shows an arrangement of cylindrical passages 5 formed in the structure 4. In this case every passage 5 is defined by walls forming segments of the cylindrical passage extending through the structure. In each of these examples the passages are closely arranged, forming a close packed arrangement of passages in the structure.

In the following an example of fabrication of a miniaturised electrochemical sensor is disclosed. The structure supporting the working electrode is fabricated by providing a double side polished 100 mm diameter, 300 micrometers thick silicon wafer. The silicon wafer is spin coated with 6 micrometers thick layer of a photoresist (AZ 9260). The wafer with the photoresist layer is then soft baked on a hot plate for 2 min and thereafter exposed with UV light at an intensity of 300 mW/cm$^2$ for 15 s, through a lithography mask. The photoresist is then developed using developer 2401 for 3 min in order to define a pattern. The pattern defines the walls and passages of the structure 4. The structure is then etched using deep reactive ion etching for 1.5 hrs to form a grid structure having walls and passages.

The etched silicon wafer is then transferred to an atomic layer deposition chamber (Beneq TFS 200). Here a 10 nm layer of $Al_2O_3$ is deposited on to the structure followed by a 10 nm thick platinum layer. The wafer is then diced into chips of dimensions about 10×10 mm$^2$.

The chips with the structures are then dipped in 5% Nafion solution (SE-5112, Dupont) and desiccated in a low pressure chamber. This low pressure treatment helps in removing the air in the micropores and thus facilitates the deposition of Nafion in the passages. The Nafion coated chip is then removed from the low pressure chamber and dried in air for 2 hrs. The Nafion coated grid structure is used as the working electrode in the sensor.

The fabrication of the counter and reference electrode is carried out on a 2 mm thick polycarbonate (PC) substrate. Silver of thickness 500 nm is deposited on one side of the PC substrate using e-beam evaporation. The silver is then patterned to define counter and reference electrode. The reference electrode is oxidized to $AgO_2$ by applying a voltage of 1.0 V on the silver electrode, which is the anode by using a platinum electrode as the cathode.

The chip with the working electrode is fastened, e.g. glued, on top of the counter and the reference electrode. The assembly may thereafter be submerged into a liquid electrolyte solution and put in a vacuum desiccator to fill the chamber between the working and the counter/reference electrode. The liquid electrolyte now ionically, thus electrically, connects the working, counter and the reference electrodes.

During operation of the electrochemical sensor, a gas to be analyzed is provided at the first surface of the sensor. The potential at the working electrode is kept at +0.7 V with respect to the $Ag/AgO_2$ reference electrode. At this potential NO is oxidized giving the following reaction:

$$NO + 2H_2O \rightarrow NO_3^- + 4H^+ + 3e^-$$

The counter electrode enables a current to flow through the sensor cell. The working potential, electrolyte and electrode materials are so chosen that the gas being measured is oxidized at the working electrode. The Nafion layer acts as a diffusion layer that permits an interaction between the gas, electrode and liquid. As the oxidization takes place at the working electrode, oxygen is normally reduced to water at the counter electrode. The resulting current which flows through the sensor is directly proportional to the gas concentration. Thus the oxidation of the analyte, in this case NO, at the working electrode results in a current that is detected by using a potentiostat that comprises a transimpedance amplifier. It is also used for maintaining a constant potential between the working and the reference electrode.

The fabricated sensor has been tested to characterize levels of 0 to 100 ppb of NO in $N_2$ gas. The detection limit (S/N=2) was estimated to be 0.3 ppb and the sensitivity was measured to be 4 microA/ppm/cm$^2$. The response and the recovery time of the sensor (time to return to 90% of starting signal) were measured to be 6 s.

The invention claimed is:

1. A miniaturised electrochemical sensor for detection of a component in a gas, comprising a reference electrode, a counter electrode, a structure comprising a plurality of passages extending from a first surface to a second surface and delineated by walls extending along the passages, a working electrode which covers the walls of the structure from the first to the second surface and a layer of an ionomer covering at least part of the working electrode along the walls of the structure wherein the layer of ionomer is in ion conducting contact with the electrodes.

2. The sensor according to claim 1 wherein the passages have an aspect ratio of at least 0.25, at least 1, at least 4, at least 10, at least 20 or at least 50.

3. The sensor according to claim 1 wherein the passages have a cross-sectional dimension in the range of 1-300 micrometers or in the range of 10-150 micrometers.

4. The sensor according to claim 1 wherein the surface area of the ionomer layer is in the range of 2000-2 cm$^2$ per cm$^2$ foot print area or in the range of 1000-10 cm$^2$ per cm$^2$ foot print area or in the range of 200-20 cm$^2$ per cm$^2$ foot print area.

5. The sensor according to claim 1 wherein the first surface is exposed to the gas.

6. The sensor according to claim 1 wherein the structure is a porous structure, whereby the passages are formed as pores.

7. The sensor according to claim 6 wherein the pores extend in parallel throughout the structure.

8. The sensor according to claim 6 wherein the pores are provided in a close packed arrangement.

9. The sensor according to claim 8 wherein the close packed arrangement is at least one of a hexagonal arrangement, a rectangular arrangement, a quadratic arrangement and a triangular arrangement.

10. The sensor according to claim 1 wherein the ionomer is a sulfonated tetrafluoroethylene based fluoropolymer-copolymer.

11. The sensor according to claim 1 wherein the ionomer is a proton conductor.

12. The sensor according to claim 1 wherein the thickness of the ionomer layer covering the working electrode is in the range of 10-2000 nm or 100-1000 nm or 300-700 nm.

13. The sensor according to claim 1 wherein the ionomer comprises a nanostructured solid material.

14. The sensor according to claim 1 further comprising a liquid electrolyte in contact with the layer of ionomer and the reference and counter electrodes.

15. The sensor according to claim 14 wherein the first surface is exposed to the gas and wherein the second surface is in contact with the liquid electrolyte.

16. The sensor according to claim 15 wherein the sensor comprises an enclosure for a volume of the liquid electrolyte.

17. The sensor according to claim 1 wherein the structure is formed by micromachining.

18. The sensor according to claim 17 wherein the structure is formed by micromachining of a silicon material.

19. The sensor according to claim 1 wherein the working electrode comprises a material selected from the group consisting of platinum, gold, palladium, carbon and ruthenium.

20. The sensor according to claim 1 wherein the working electrode is insulated from the structure by an insulating layer.

21. The sensor according to claim 20 wherein the insulating layer comprises a material selected from the group consisting of $Al_2O_3$, $SiO_2$, $HfO_2$ and $LaO$.

22. The sensor according to claim 1 wherein the component in the gas is NO.

23. A device for measuring content of NO in exhaled breath comprising a miniaturised electrochemical sensor according to claim 1.

24. A method of fabricating a miniaturised electrochemical sensor according to claim 1, comprising providing a structure comprising a plurality of passages extending from a first surface to a second surface and delineated by walls extending along the passages, covering the walls of the structure from the first to the second surface with a working electrode, depositing a layer of ionomer covering at least part of the working electrode along the walls of the structure.

25. The method according to claim 24 wherein the miniaturised electrochemical sensor is batch fabricated using silicon microfabrication and wherein the structure is provided by etching a silicon material.

26. The method according to claim 24 wherein the layer of ionomer is deposited by dip coating and desiccated under low pressure.

27. The method according to claim 24 wherein the working electrode is deposited by atomic layer deposition.

28. The method according to claim 24 wherein the method comprises:

providing a liquid electrolyte in electrical contact with the working electrode, providing a reference electrode and a counter electrode in electrical contact with the liquid electrolyte.

29. The method according to claim 28 wherein the structure is provided by deep reactive ion etching a silicon material.

* * * * *